(12) United States Patent
Hwang et al.

(10) Patent No.: US 10,980,944 B2
(45) Date of Patent: Apr. 20, 2021

(54) SYRINGE TIP CAP

(71) Applicant: Becton, Dickinson and Company, Franklin Lakes, NJ (US)

(72) Inventors: Charles G. Hwang, Wellesley, MA (US); Roger Groskopf, Saddle Brook, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 386 days.

(21) Appl. No.: 15/202,953

(22) Filed: Jul. 6, 2016

(65) Prior Publication Data

US 2016/0310671 A1 Oct. 27, 2016

Related U.S. Application Data

(63) Continuation of application No. 10/691,385, filed on Oct. 22, 2003, now Pat. No. 9,415,168, which is a continuation-in-part of application No. 29/180,313, filed on Apr. 22, 2003, now Pat. No. Des. 493,526.

(51) Int. Cl.
*A61M 5/31* (2006.01)

(52) U.S. Cl.
CPC ... *A61M 5/3134* (2013.01); *A61M 2005/3104* (2013.01); *A61M 2205/586* (2013.01)

(58) Field of Classification Search
CPC .................... A61M 5/3134; A61M 2005/3104
USPC ....................................................... 604/187
See application file for complete search history.

(56) References Cited

U.S. PATENT DOCUMENTS

| | | | |
|---|---|---|---|
| 2,585,527 A | | 2/1952 | Adams |
| 3,344,786 A | | 10/1967 | Berg et al. |
| 3,581,926 A | * | 6/1971 | Roder ................ B65D 41/0471 215/330 |
| 3,664,338 A | | 5/1972 | Knox et al. |
| 3,718,139 A | | 2/1973 | Hanford |
| 3,777,655 A | | 12/1973 | Ainsworth |
| 3,916,894 A | | 11/1975 | Cloyd |
| 3,986,645 A | | 10/1976 | Baldwin et al. |
| 4,006,837 A | | 2/1977 | Gates et al. |
| 4,043,334 A | | 8/1977 | Brown et al. |

(Continued)

FOREIGN PATENT DOCUMENTS

FR 2570055 3/1986

OTHER PUBLICATIONS

Communication Pursuant to Article 96(2) EPC for European Patent Application No. 03 773 313.6-1257 dated May 22, 2007 (6 pages).

*Primary Examiner* — Brandy S Lee
*Assistant Examiner* — Nidah M Hussain
(74) *Attorney, Agent, or Firm* — The Webb Law Firm

(57) ABSTRACT

A tip cap is provided comprising a base portion having an upper surface and a lower surface, a body having a top wall with a non-circular cross-section extending from the upper surface, and a shaft extending from the lower surface. A syringe assembly is provided comprising a syringe comprising a barrel, and a syringe tip, extending through the barrel and a connector provided on the syringe tip. The syringe assembly further comprises a tip cap for sealingly covering the syringe tip and comprising a base portion having an upper surface and a lower surface, a body having a top wall with a non-circular cross-section extending from the upper surface, and a shaft extending from the lower surface having connection means for attaching to the syringe tip.

22 Claims, 8 Drawing Sheets

(56) References Cited

U.S. PATENT DOCUMENTS

| | | | | |
|---|---|---|---|---|
| 4,202,334 | A | 5/1980 | Elson | |
| 4,238,042 | A | 12/1980 | Hatakeyama et al. | |
| 4,280,632 | A * | 7/1981 | Yuhara | B65D 41/02 215/331 |
| 4,286,591 | A | 9/1981 | Raines | |
| 4,402,420 | A | 9/1983 | Chernack | |
| 4,535,906 | A * | 8/1985 | Rowekamp | B65D 41/0471 215/329 |
| 4,535,909 | A | 8/1985 | Rowekamp | |
| 4,571,242 | A | 2/1986 | Klein et al. | |
| 4,597,501 | A * | 7/1986 | Gueret | B65D 41/0435 215/330 |
| 4,742,910 | A * | 5/1988 | Staebler | A61M 5/3213 206/365 |
| D302,206 | S | 7/1989 | McAllister et al. | |
| 4,898,588 | A | 2/1990 | Roberts | |
| 4,926,915 | A | 5/1990 | Deussen et al. | |
| 4,932,937 | A | 6/1990 | Gustavsson et al. | |
| 4,979,945 | A | 12/1990 | Wade et al. | |
| 4,998,922 | A * | 3/1991 | Kuracina | A61M 5/3275 604/192 |
| D321,251 | S * | 10/1991 | Jepson | D24/112 |
| 5,108,889 | A | 4/1992 | Smith et al. | |
| D327,318 | S | 6/1992 | Dudar et al. | |
| 5,135,513 | A * | 8/1992 | Meyer | A61M 5/34 604/240 |
| 5,183,469 | A * | 2/1993 | Capaccio | A61M 5/3213 206/365 |
| 5,322,515 | A | 6/1994 | Karas | |
| 5,334,151 | A * | 8/1994 | Santilli | A61M 5/3213 206/365 |
| 5,533,980 | A * | 7/1996 | Sweeney | A61M 5/178 604/110 |
| 5,634,496 | A | 6/1997 | Grabner, Jr. | |
| D381,965 | S | 8/1997 | Atkinson | |
| 5,725,507 | A | 3/1998 | Petrick | |
| D395,502 | S * | 6/1998 | Deily | D24/112 |
| 5,782,804 | A | 7/1998 | McMahon | |
| 5,807,345 | A | 9/1998 | Grabenkort | |
| 5,810,792 | A * | 9/1998 | Fangrow, Jr. | A61M 39/045 285/319 |
| 5,925,029 | A | 7/1999 | Jansen et al. | |
| 5,944,698 | A * | 8/1999 | Fischer | A61M 5/3134 604/236 |
| 5,945,957 | A | 9/1999 | Chin-Loy et al. | |
| 5,992,656 | A * | 11/1999 | Dujardin | B29C 45/14598 215/330 |
| D425,197 | S * | 5/2000 | Comer | D24/130 |
| D431,864 | S * | 10/2000 | Jansen | D24/129 |
| D447,797 | S | 9/2001 | Odell et al. | |
| D447,799 | S * | 9/2001 | Jun | D24/130 |
| 6,309,375 | B1 | 10/2001 | Glines et al. | |
| D457,954 | S * | 5/2002 | Wallace | D24/130 |
| 6,632,199 | B1 * | 10/2003 | Tucker | A61M 5/3134 604/192 |
| 6,695,829 | B2 | 2/2004 | Hellstrom et al. | |
| 6,875,205 | B2 | 4/2005 | Leinsing | |
| D568,468 | S * | 5/2008 | Sudo | D24/130 |
| D568,469 | S * | 5/2008 | Sudo | D24/130 |
| D570,478 | S * | 6/2008 | Sudo | D24/130 |
| D581,047 | S * | 11/2008 | Koshidaka | D24/130 |
| D736,914 | S * | 8/2015 | Schultz | D24/129 |
| D736,915 | S * | 8/2015 | Schultz | D24/129 |
| 9,415,168 | B2 * | 8/2016 | Hwang | A61M 5/3134 |
| 2002/0174864 | A1 | 11/2002 | Alchas | |
| 2004/0097882 | A1 | 5/2004 | DiBiasi et al. | |
| 2004/0116869 | A1 | 6/2004 | Heinz et al. | |
| 2004/0215148 | A1 * | 10/2004 | Hwang | A61M 5/3134 604/187 |
| 2013/0281970 | A1 * | 10/2013 | Erickson | A61M 5/3243 604/506 |
| 2016/0121097 | A1 * | 5/2016 | Steele | F16L 35/00 138/89 |
| 2016/0310671 | A1 * | 10/2016 | Hwang | A61M 5/3134 |
| 2017/0189618 | A1 * | 7/2017 | Ward | A61M 5/1782 |

* cited by examiner

SYRINGE TIP CAP

CROSS-REFERENCE TO RELATED APPLICATIONS

This application is a continuation of U.S. Utility application Ser. No. 10/691,385, filed on Oct. 22, 2003, which is a continuation-in-part of U.S. Design application No. 29/180,313, filed on Apr. 22, 2003, which has issued as U.S. Design Pat. No. D493526, the entirety of all of which are incorporated by reference herein.

BACKGROUND OF THE INVENTION

1. Field of the Invention

This invention relates to a tip cap for closure of the opening of a liquid filled container, and more particularly, to a tip cap for a syringe.

2. Description of Related Art

Conventional syringes include a barrel having an open proximal end and an opposed distal end. A cylindrical wall extends between the ends and defines a substance retaining chamber. A tip, sometimes referred to as a luer, projects from the distal end of the syringe barrel and includes a narrow passage, which communicates with the substance-retaining chamber of the barrel. A plunger is inserted into the open proximal end of the syringe barrel for sliding fluid-tight engagement with the cylindrical chamber wall. Sliding movement of the plunger in a distal direction urges fluid in the chamber through the passage in the tip. Conversely, sliding movement of the plunger in a proximal direction draws fluid through the passage in the tip and into the chamber of the syringe barrel.

Such syringes may further include a needle assembly with a needle cannula having a proximal end, a pointed distal end and a lumen extending axially therethrough. The needle assembly commonly includes a hub which is securable to the syringe barrel for selectively placing the lumen of the needle cannula in fluid communication with the passage through the tip of the syringe barrel. The needle assembly may be removably or fixedly mounted to the tip of the syringe barrel.

Medications that are pre-filled into a syringe barrel must be sealed to prevent contamination or loss of the medication prior to use. Seals also prevent health care workers from being needlessly exposed to medications. Where a needle is not staked to the syringe body, the prior devices have included stoppers or closures mounted over the tip at the distal end of the syringe barrel, referred to as tip caps, to prevent leakage and to avoid contamination of the medication. When a pre-filled syringe is capped with a tip cap, it is especially important that a good seal be maintained. This is usually achieved by tightly affixing the tip cap to the syringe. However, when overly tightened the tip cap can be difficult to remove or may be damaged. Furthermore, a pre-filled syringe may be autoclaved after filling and capping to ensure a sterile package for the contents. The autoclaving procedure however, can also have the side effect of interactions between the tip cap to the syringe, thereby further increasing the difficulty in removing the cap.

The prior art tip cap is removed from the syringe tip shortly prior to usage of the syringe, and the hub of the needle assembly is securely engaged with the luer and/or luer collar or other mounting means adjacent the exposed tip of the syringe barrel. For example, the needle hub may be threadedly engaged within a luer collar such that the lumen of the needle cannula communicates with the exposed tip of the syringe barrel, such as with the configuration sold by the assignee herein under the trademark "Luer-Lok".

Current tip caps used to seal the liquid opening of the syringe barrel, are typically a one-piece design having a circular cap wall design. The mechanical advantage of a screw-type threaded cap is translation of a rotational force to an axial force, resulting in wedging the sealing mechanism of the tip cap onto the luer of the container, and forming a tight seal due to the interference fit between the sealing mechanism and the luer. With the current tip caps, the torque required to attach and remove the tip cap is generated when the user applies a gripping force to the outside of the cap to rotate the cap on and off the syringe.

A problem associated with the prior art tip cap design has been the user must apply a gripping force to grasp the circular cap by exerting a force normal to the cap walls at the point of contact with sufficient force to hold the cap from slipping, as well as applying a twisting force (a torque) for rotating the cap about its axis. This can be difficult for some users who lack dexterity or strength especially considering the small size of the typical tip cap or in the case where the tip cap is in excessively tight engagement with the syringe barrel. The difficulty in using tip caps according to prior art design is that the user must exert forces on the tip cap at right angles to both grasp and rotate the tip cap simultaneously.

A need exists, therefore, for an improved syringe tip cap where the ability to attach and detach the tip cap is made easier by providing a tip cap that is easier to grip while simultaneously applying torque to rotate the tip cap. In particular, it would be advantageous to provide a tip cap with a non-circular shaped gripping surface that Provides the user with a surface to grip the cap and apply force to the tip cap tangential to the axis of rotation without having to also apply a gripping force.

SUMMARY OF THE INVENTION

In contrast to the prior devices discussed above, it has been found that a tip cap which provides the user with enhanced mechanical advantage for rotating the cap in order to affix it to a syringe can be constructed in accordance with the present invention. Specifically, the tip cap of the present invention includes a non-circular cross-sectional shape that provides a gripping surface for providing the user with extra leverage to rotate the cap.

The present invention provides a syringe tip cap assembly for closing a syringe such as a pre-filled syringe barrel. The tip cap includes a tip cap body having a non-circular top wall, a base sealing surface and a depending shaft, which may be threaded, for attachment of the tip cap to a syringe. The opening and closing of a threaded tip cap is accomplished by imparting torque to the cap tangential to the axis of rotation to cause the cap to rotate and thereby open or close by engaging the helical threads of the cap and container to raise or lower the cap. The force imparted to the cap is applied by the user by gripping the perimeter of the cap.

The tip cap of the present invention makes it easier and more effective for the user to apply the rotational force needed to turn the cap and thus open and close it. The non-circular shaped gripping area provides a surface for the application of force directly tangential to the axis or rotation of the cap. The force is applied to the tip cap tangential to the axis of rotation at a distance from the axis. Therefore, the non-circular tip cap acts as a lever arm to multiply the force applied to the tip cap. In addition, because of the non-circular shape, the user need not apply a normal force to the sides of the cap in order to grip the cap as is the case with prior art designs.

An advantage of the tip cap of the present invention is that it provides the user with increased mechanical advantage for rotating the cap.

Another advantage of the tip cap of the present invention is that the outer surface of the tip cap contains features to enhance handling and grip for the user, and to provide a comfortable gripping surface that will not cut into the users fingers.

The present invention is therefore directed to a tip cap comprising a base portion having an upper surface and a lower surface, a body having a top wall with a non-circular cross-section extending from the upper surface, and a hollow shaft extending from the lower surface, attaching to a syringe barrel.

BRIEF DESCRIPTION OF THE DRAWINGS

The various features, objects, benefits, and advantages of the present invention will become more apparent upon reading the following detailed description of the preferred embodiment(s) along with the appended claims in conjunction with the drawings, wherein like reference numerals identify like components throughout, and:

DETAILED DESCRIPTION OF THE INVENTION

Figure 1:
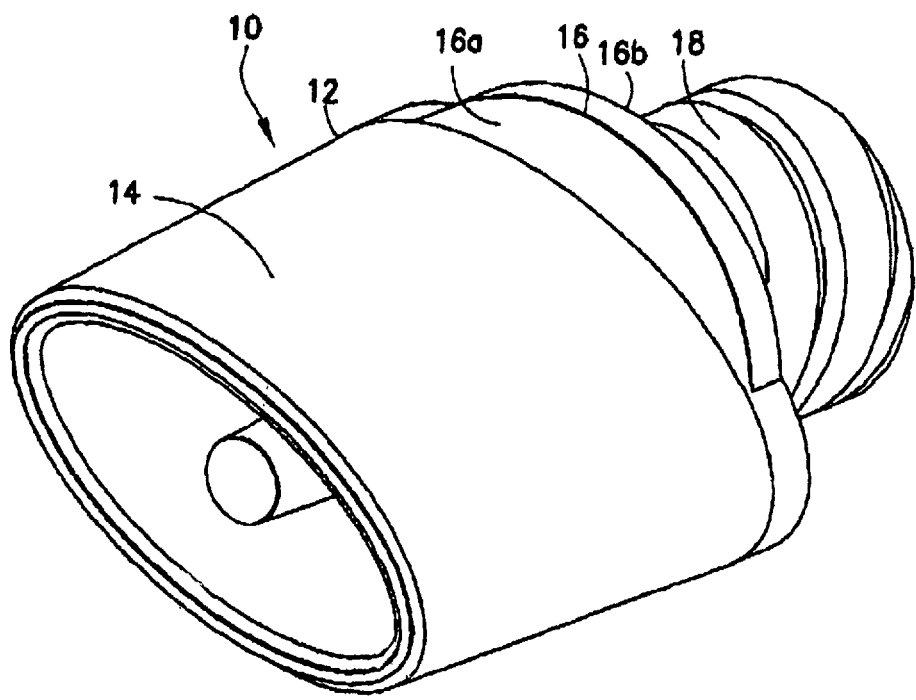
FIG. 1 is a perspective view of a tip cap according to an embodiment of the present invention.

Referring now to the drawings, FIG. 1 shows a tip cap according to the present invention. In particular, FIG. 1 shows a tip cap 10. As can be seen, tip cap 10 includes a cap body 12 having a top wall 14 and a depending sealing base 16, and further includes a shaft 18 for connecting to and disconnecting from a syringe 200. The shaft 18 and the cap body 12 form a single unitary tip cap for receiving a force imparted to the top wall 14 which causes the tip cap 10 to rotate and connect to a syringe body. The top wall 14 is a non-circular tubular structure, extending upwardly, or in a first direction, from the sealing base 16. The sealing base 16 is a substantially flat surface having an upper surface 16a defining a plane and lower surface 16b. Top wall 14 is rigidly joined to the upper surface 16a, preferably about at least the majority of its perimeter, and the shaft 18 is rigidly joined to the lower surface 16b.

Figure 2:
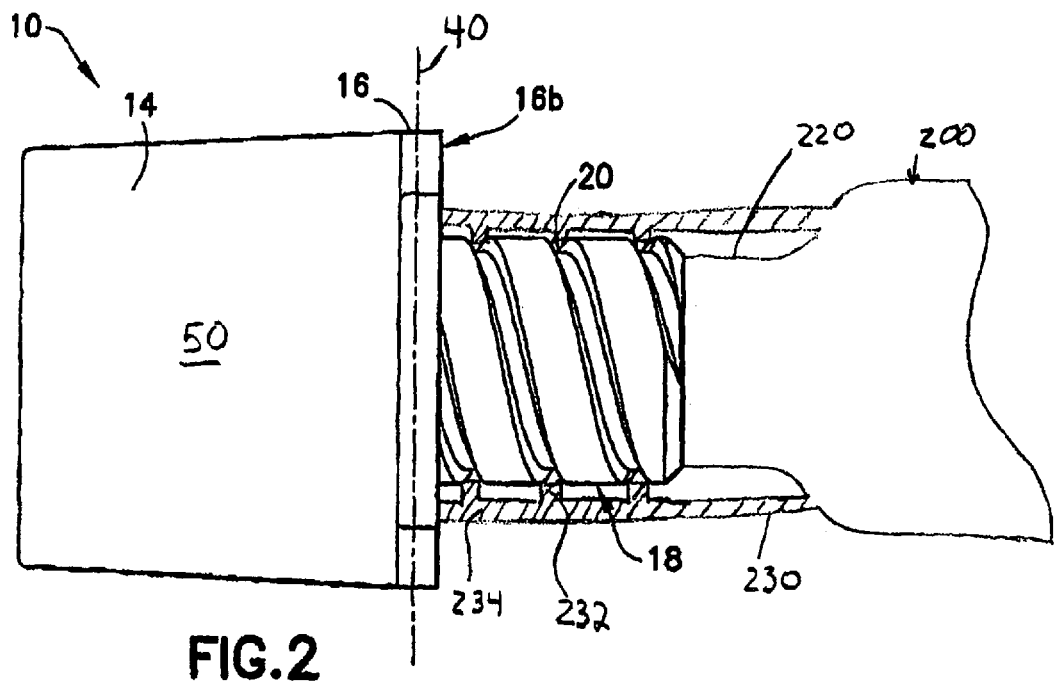
FIG. 2 is a first side view of the tip cap of FIG. 1.

FIG. 2 depicts the tip cap 10 according to the present invention as viewed from the side along a major axis 40 of the cap body 12. As seen in FIG. 2, the top wall 14 is preferably coextensive with the sealing base 16 along major axis 40 of the cap body 12. Also shown is the shaft 18 extending downwardly, or in a second direction, from the sealing base 16. The shaft 18 is configured to attach to the luer tip 220 of a syringe 200. A connector 230 may be provided at the tip 220 of the syringe 200 such as, for example, a luer locking collar. The connector 230 may include internally defined threads 232 extending from wall portion 234. Preferably, the shaft 18 has threads 20 for engaging complementary threads 232 of the connector 230. The threads 20 are arranged to provide adequate locking for a given angular displacement of the tip cap 10. With this arrangement a seal is defined about the luer tip 220 by tight contact with the interior of the shaft 18. The threads 20 can be configured to cooperate with any known threaded configuration and provide additional holding force to maintain the position of the tip cap 10 relative to the luer tip 220. Alternatively, the shaft 18 may be configured with any other known connection configuration, including, but not limited to, a slip luer connection.

Figure 3:
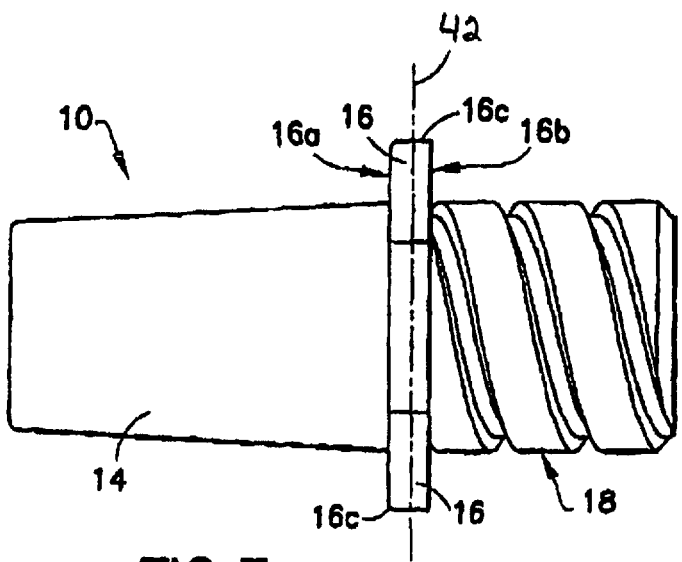
FIG. 3 is a second side view of the tip cap of FIG. 1.

FIG. 3 depicts the tip cap 10 according to the present invention as viewed from the side along minor axis 42 of the tip cap body 12. Preferably, as seen in FIG. 3, portions 16c of the sealing base 16 extend radially outwardly along the minor axis 42 of the top wall 14. The portions 16c may act as shields against excessive downward movement of a user's fingers relative to the tip cap 10. With the portions 16c, inadvertent contact with an associated syringe body, particularly a portion that has been sterilized, can be avoided.

Figure 4:
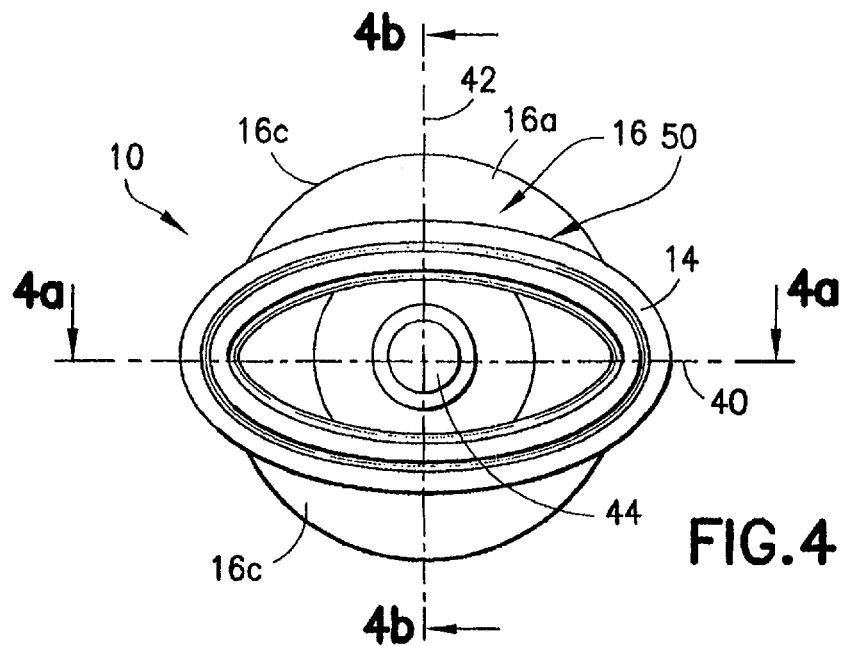
FIG. 4 is top view of the tip cap of FIG. 1.

FIG. 4 depicts the tip cap 10 according to the present invention as viewed from the top (i.e., substantially perpendicular to the plane defined by the upper surface 16a). In this view, the substantially non-circularity of the top wall 14 is shown. Thus, a cross-sectional view taken along a plane that is substantially parallel to the plane defined by the upper surface 16a will be substantially con-circular. Preferably, the top wall 14 is elongated, having the major axis 40 and the minor axis 42. The top wall 14, according to the present invention, will preferably be formed in a non-circular elliptical shape, thereby providing an elongated gripping surface 50 defined by the top wall 14. The gripping surface 50 (see, e.g., FIG. 2) need not be limited to the surface defined along the major axis 40, but can include the surface defined along the minor axis 42. In addition, the gripping surface 50 may include a surface that extends along both the major and minor axes 40, 42. As will be described with reference to FIG. 9, the non-circular shaped top wall 14 allows a user to grasp the tip cap 10 and apply a rotational force (torque) to the tip cap 10, without having to simultaneously provide a tight grip on the tip cap 10. In addition, with the non-circular shaped top wall 14 of the present invention, the tip cap 10 is unable to roll away from a user, as is often the case with circularly shaped prior art tip caps.

Figure 4A:
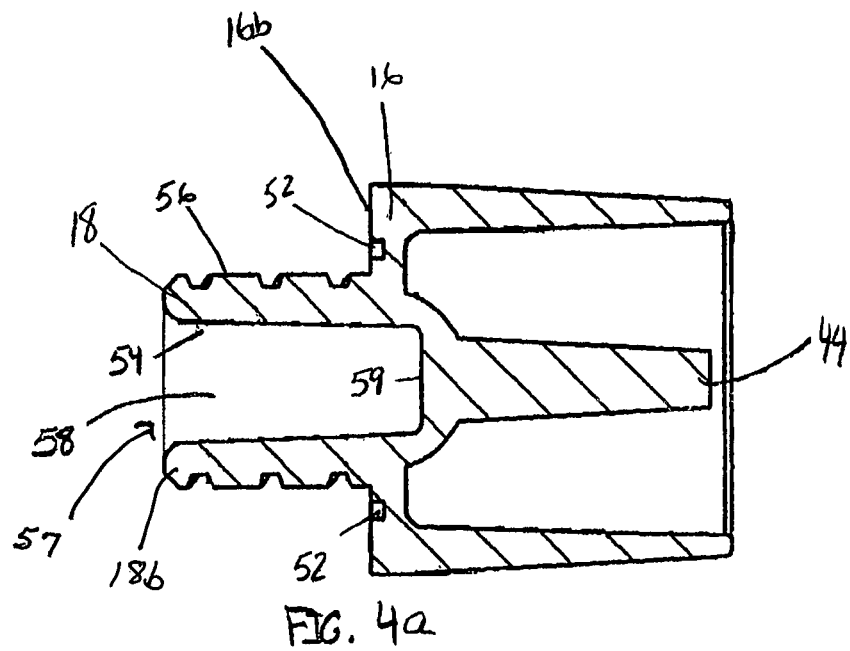
FIGS. 4a and 4b are a cross-sectional views of the tip cap according to the present invention along sections lines 4a-4a and 4b-4b of FIG. 4.
Figure 4B:
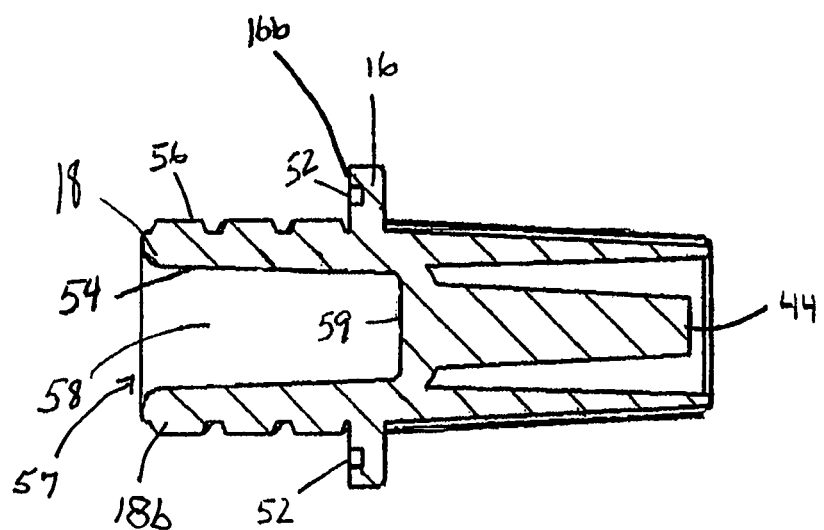

FIGS. 4a and 4b depict cross-sectional views of the tip cap according to the present invention along section lines 4a-4a and 4b-4b of FIG. 4. As shown in cross sections 4a-4a and 4b-4b, shaft 18 is preferably hollow having inner and outer walls 54 and 56, respectively, to define a hollow portion, and being open or having an opening, as generally shown by 57, at the bottom end 18b of the shaft 18. Preferably, a well 58 is defined to at least partially extend through the sealing base 16 shaped and configured to receive a luer tip which would extend through the opening 57 and into the well 58 and beyond the bottom face 16b with the tip cap 10 being mounted to the syringe 200, as depicted in FIG. 2. The well 58 may be shaped internally to match the general shape of the tip or luer. For example, as shown in FIG. 4*a*, the inner end 59 of well 58 has a flat profile, complementary to that of the part of the syringe to which it is secured. External surface 44 of the well 58 can be generally conical, as shown to advantageously be relied upon in releasing the product from a mold. Also shown are depressions 52 recessed into the bottom face 16*b*.

Figure 5:
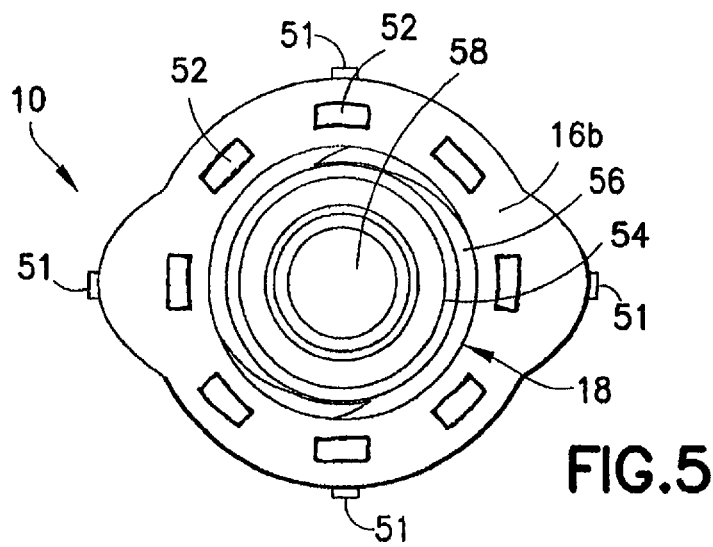
FIG. 5 is bottom view of the tip cap of FIG. 1.

FIG. 5 depicts a bottom view of the tip cap 10 according to the present invention. Shown in FIG. 5 is the bottom face 16*b* of sealing base 16. To facilitate removal of the tip cap 10 from a molding machine, one or more depressions 52 may be recessed into the sealing base 16, such as shown, recessed into the bottom face 16*b*.

It should also be noted that one or more outwardly extending nubs or tabs 51 may be formed extending in cantilevered fashion from the edge of sealing base 16 to facilitate handling of the tip cap 10 according to the present invention by machinery. The nubs or tabs 51 allow machinery, such as "forgiving" machines to handle the tip cap 10 without engaging the gripping surface 50. Accordingly, a more straightforward machine arrangement to engage nubs or tabs 51, may be utilized than if the gripping surface 51 needed to be handled. While four such nubs or tabs are shown in FIG. 5, it would be understood by one skilled in the art to modify the number and placement of such structures as needed.

Figure 7:
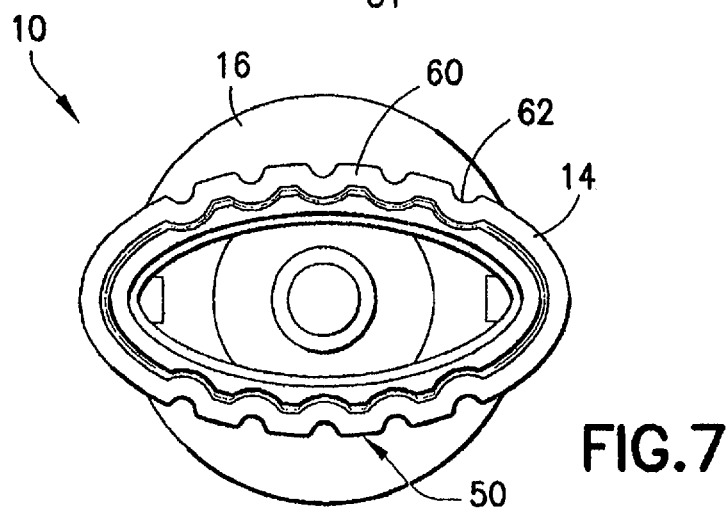
FIG. 7 is top view of the tip cap of FIG. 6.
Figure 6:
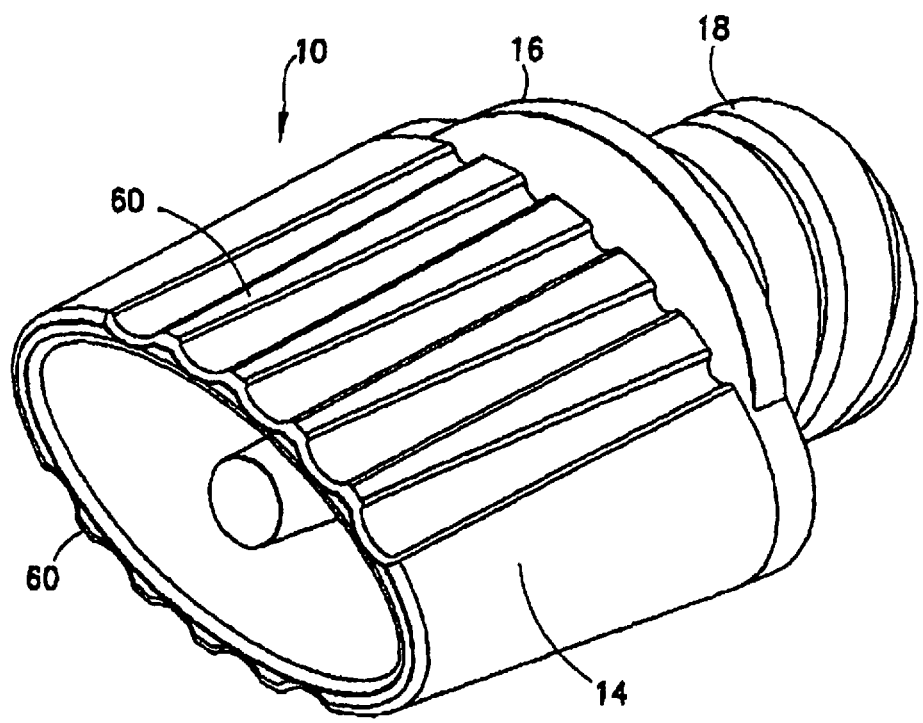
FIGS. 6 and 6a respectively are perspective views of a tip cap according to different embodiments of the present invention with a textured top wall.
Figure 6A:
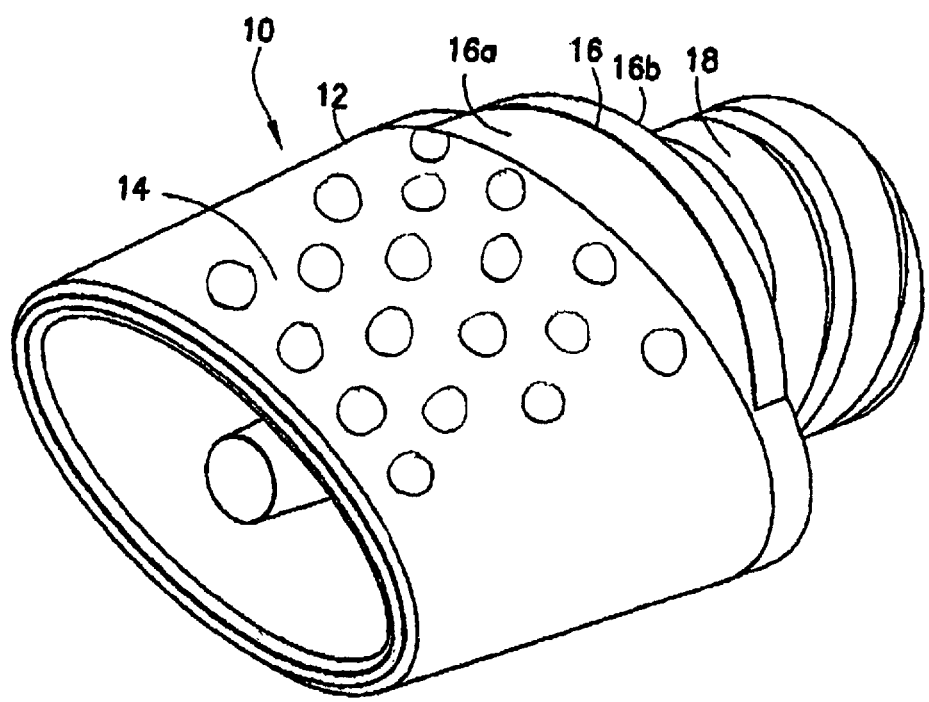

As shown in FIGS. 6, 6*a* and 7, the tip cap 10 may have a textured top wall 14. For example, the tip cap 10 depicted in FIG. 6 includes a plurality of ribs 60 on the exterior of the top wall 14. The ribs 60 provide texture to the top wall 14 exterior surface in order to provide the user with an enhanced gripping surface. As will be apparent to one skilled in the art and from the disclosure provided herein, the placement and number of ribs can be varied to provide the user with the desired tactile sensation and grip characteristics. In addition, while the surface texture in this embodiment is shown as ribs, the surface of top wall 14 could alternately have other types of textures or exterior structures to provide tactile sensation and additional grip. As will be recognized by those skilled in the art, and shown in FIG. 6*a*, the top wall 14 could for example alternately have dimples or any other known texture, including, but not limited to, the textures found in a library maintained under the trademark "MOLD-TECH" by Standex International Corp. of Salem, N.H., U.S.A.

Turning now to FIG. 7, the profile of ribs 60 can be seen. Preferably, ribs 60 are located on the exterior of top wall 14 along the longer wall portions (disposed along the major axis 40). In this way the ribs 60 are located where a user would grip the tip cap 10 in order to rotate the tip cap. In addition, the ribs 60 further provide a surface that would not cut into the fingers of the user. As seen in FIG. 7, the cross-sectional profile of the body 12 of the tip cap 10 is elliptical with a plurality of grooves 62 defined in the gripping surface 50. Thus, the elliptical gripping surface 50 is free of protrusions that would press into the user's fingers under high torque on/off situations. Alternate texture could also be located in the same location as depicted in FIG. 7.

Figure 8:
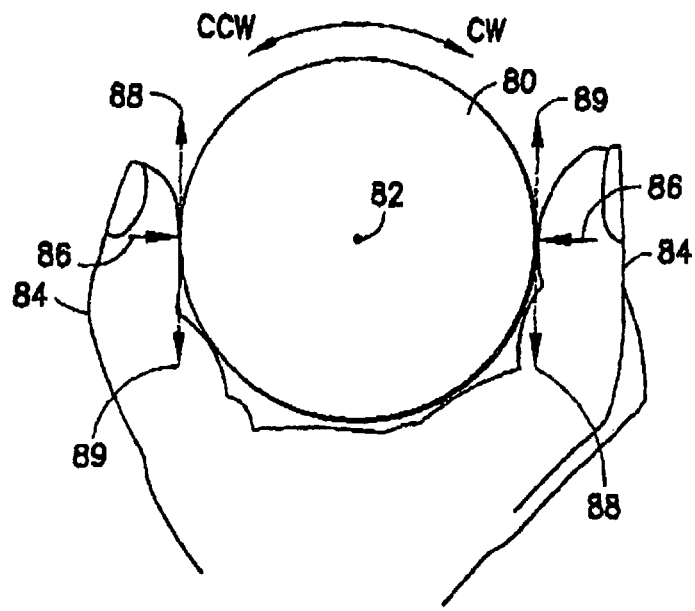
FIG. 8 is a force diagram for the rotation of a tip cap according to a prior art design.

Turning now to FIG. 8, there is shown a force diagram that illustrates the application of forces by a user to rotate a prior art cap about its central axis. FIG. 8 shows a circular top wall 80 of a prior art tip cap, with the rotational center point 82 (i.e., the intersection of the major and minor axes (which, for prior art devices are the same)) and which is being grasped by a user's hand 84. User's hand 84 is shown exerting a gripping force 86, normal to the surface of the top wall 80. In order to rotate the cap the user must also apply a rotational force (torque) to the tip cap. For example, to rotate the tip cap in a clockwise direction, the user would apply force 88 tangential to the top wall 80. Likewise, to rotate the tip cap in a counterclockwise direction, the user would apply force 89 tangential to the top wall 80 axis of rotation. The amount of gripping force 86 the user must apply is proportional to the rotational force needed to turn the tip cap. For example, a user must grip the tip cap more tightly when turning a tip cap that has been tightly closed as opposed to a tip cap that has been less tightly closed.

Figure 9:
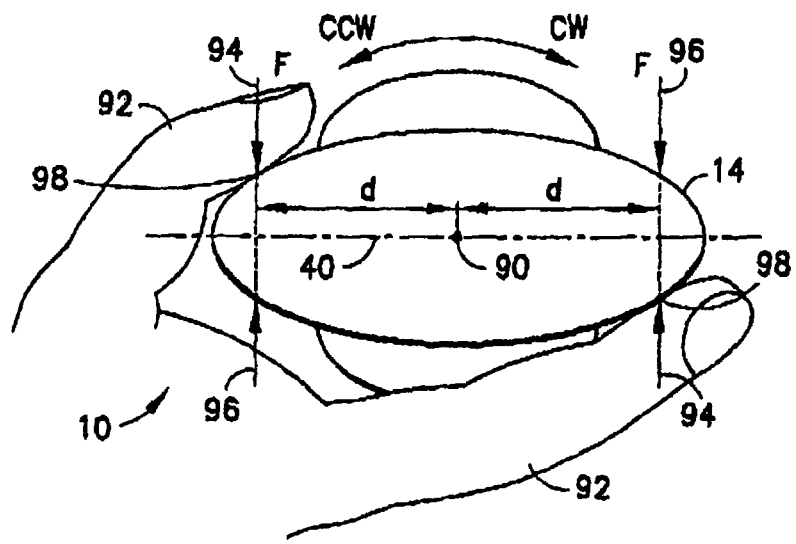
FIG. 9 is a force diagram for the rotation of a tip cap according to the present invention.

In FIG. 9, there is shown a force diagram depicting the application of force by a user to rotate the tip cap 10 according to the present invention. FIG. 9 shows a top view of the tip cap 10 according to the present invention, depicting a non-circular top wall 14 being grasped by a user's hand 92. The rotational center point 92 (which is the intersection of the major and minor axes (which, for the present invention are different)) is also shown. To rotate the cap in a counter clockwise direction, the user would apply forces 94 to the top wall 14. Likewise, to rotate the tip cap in a clockwise direction, the user would apply forces 96 to the top wall 14. In contrast to prior art designs, the user of the tip cap 10 according to the present invention merely applies a rotational force to the tip cap 10 to threadedly engage or disengage the tip cap; but a large gripping force is not required.

More particularly, a tip cap is opened or closed by imparting a force to the tip cap sufficient to overcome the forces holding it in place on the helical threads of the cap and the complementary container, or other complementary connection configuration, whereby the cap is moved from either an open or a closed position by the rotation of the cap. The forces to rotate the threaded cap are applied tangential to the axis of rotation of the cap at a distance from the axis of rotation. As shown and described in FIG. 8, in order to rotate a prior art circular cap, it must be grasped with sufficient force to hold the cap, as well as rotate the cap about its central axis. Thus, force must be applied tangential to the axis of rotation to rotate the cap and normal to the cap surface to grasp and hold the cap. The force applied to hold the cap, is proportional to the rotational force applied thus making the application of both a gripping and rotating force more difficult, especially, for example when rotating a cap that is tightly affixed.

In contrast, the tip cap 10 according to the present invention, has an elongated gripping portion that provides the user with a lever arm to easily rotate the tip cap 10. Preferably, as depicted in FIG. 9, the user grasps the tip cap 10 at any points 98 on the top wall 14 a distance "d" from the rotational center point 90 as measured along the major axis 40. The forces 94 or 96 are exerted directly on the top wall 14. The user need not grip the tip cap 10 to prevent slipping, because, unlike a circular tip cap, the rotational forces (94 or 96) are exerted normal to the top wall 14 at the points 98. The top wall 14 acts as a lever arm of length "d" to provide mechanical advantage to rotate the tip cap 10.

Rotational force may be used to remove the tip cap 10 even where a threaded connector is not provided for a syringe body. For example, the tip cap 10 can be twisted off of a luer to which it is mounted with a slip luer connection. The torque advantage described above, therefore, is as beneficial in this context, and similar contexts, as well.

The tip cap 10 of the invention may be made of a clear molded thermoplastic material so that the syringe tip may be readily viewed through the tip cap. Representative materials include, for example, polyethylene, polypropylene, and polyvinyl chloride. Although it is within the purview of the invention to provide tip caps which are transparent, it is also within the purview of this invention to provide tip caps which are color coded.

While the tip cap 10 of the present invention has been particularly described with respect to a preferred embodiment having a non-circularly elliptical shaped top wall 14, it should be apparent to one skilled in the art and from the disclosure provided herein that various alternate embodiments of the tip cap top wall 14 are contemplated by, and within the scope and spirit of the present invention. For example, the tip cap 10 may alternately include modifications such as alternate shapes or additional gripping elements to enhance torque generation. Alternate top wall 14 shapes can include, in addition to the non-circular elliptical shape of the preferred embodiment, oval shapes, polygonal shapes, such as squares and rectangles, and other non-circular shapes that provide the desired torque-reducing characteristics of the tip cap 10 of the present invention. Furthermore, additional alternate embodiments may include the tip cap top wall 14 having radially projecting structures arranged about the top wall 14. The projecting structures provide the user with an extended gripping surface 50, which acts as a lever arm to impart additional torque to the tip cap 10 when rotated by the user, as described above in connection with the embodiments of FIGS. 1-7 and 9.

The gripping elements may alternately be arranged in such a way as to provide the user with an easily gripped surface for imparting torque to the tip cap 10. The gripping element may take various alternate forms, for example, the tip cap 10 may be made with a star shape or having radially extending structures arranged around the perimeter of the tip cap 10. Alternately, the tip cap 10 can be shaped having a square or rectangular shape.

Figure 10A:
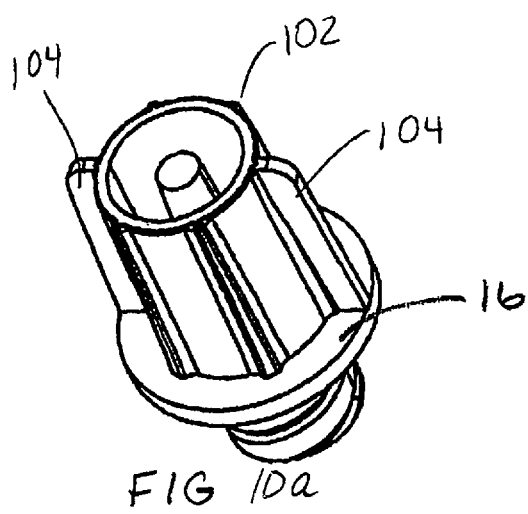
FIGS. 10a-10f are perspective views of various alternate embodiments of the present invention incorporating gripping elements.

As will be recognized by one skilled in the art and from the disclosure provided herein, various configurations are within the scope and spirit of the present invention. By way of non-limiting examples and turning to FIGS. 10a-f, alternate embodiments of the tip cap 10 according to the present invention are shown. FIG. 10a depicts an alternate embodiment wherein flanges 104 are positioned adjacent top wall 14 to provide the user with an enlarged gripping element, wherein the flanges extend outwardly from the top wall in a radial direction to the edge of sealing base 16. It should be noted however, that the dimension and size of the flanges can be varied to provide the user with a surface of sufficient size to apply force to rotate the tip cap. Preferable, the flanges 104 each have a radial length extending outwardly greater that their respective width extending in a circumferential direction. Furthermore, additional flanges 104 could be utilized in a further variation of the embodiment depicted in FIG. 10a. In addition, ribs 102 may also be provided with the embodiment of FIG. 10a, for providing an additional gripping element.

Figure 10B:
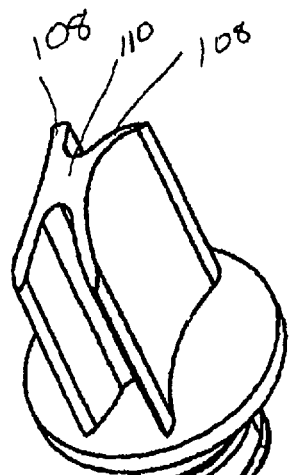
Figure 10C:
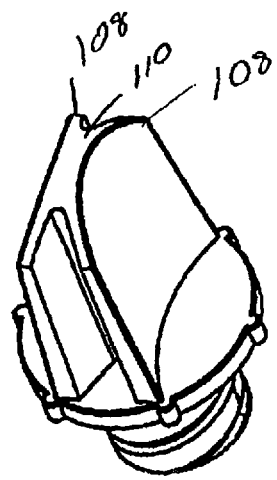

FIG. 10b depicts a further alternate embodiment of the present invention having two generally arcuate structures 108 protruding from sealing base 16. The arcuate structures 108 are rigidly connected together by support 110 that also extends from sealing base 16. The structures 108 provide an easily gripped surface for the user to impart torque to the tip cap 10. As further seen in FIG. 10c, the shape and size of the arcuate structures 108 can be varied to, for example, increase the size of the gripping surface. The embodiments of FIGS. 10b and 10c do not have a receptacle shaped cap gripping surface. For this reason these embodiments resist the retention of moisture during a steam autoclave process. In addition, they have the added advantage of not being subject to a proclivity to nest one inside another when stored in bulk.

Figure 10D:
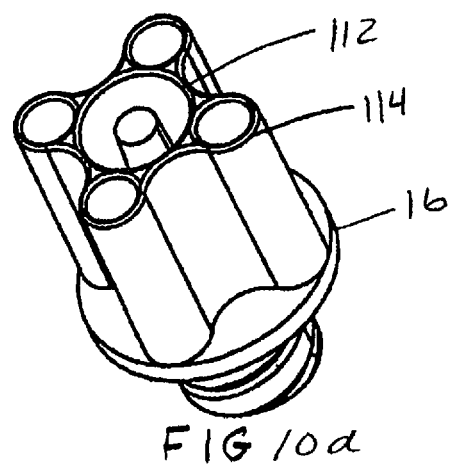

Turning now to FIG. 10d, a further alternate embodiment is depicted having a central structure 112 extending from sealing base 16, with a plurality of generally cylindrical structures 114 disposed about the central structure 112 at preferably ninety-degree intervals, for providing an easily gripped surface for the user to impart torque to the tip cap 10. FIG. 10d may be modified in accordance with the present invention by changing the number and spacing of structures 114. In addition while structures 112 and 114 are depicted as cylindrical, any other shape may be utilized, such as, for example, polygonal.

Figure 10E:
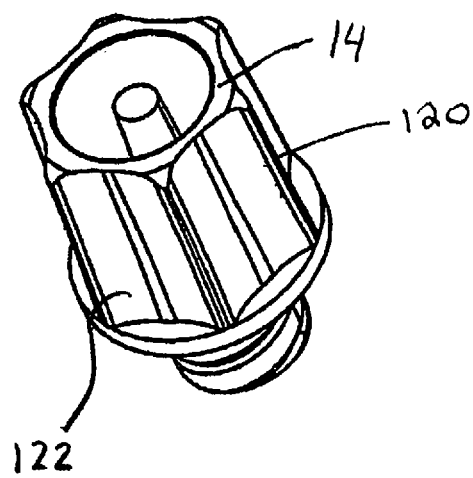

FIG. 10e depicts a further alternate embodiment wherein the tip cap 14 according to the present invention has an increased diameter top wall 14 with an undulating wall cross-section to provide a plurality of ribs 120 circumferentially spaced about top wall 14 and interconnected by a rib webs 122 to provide the user with an enhanced gripping surface by varying the angle of the surface that the user grips. In that way, the user can hold a surface that is not tangential to the rotational axis of the tip cap 10.

Figure 10F:
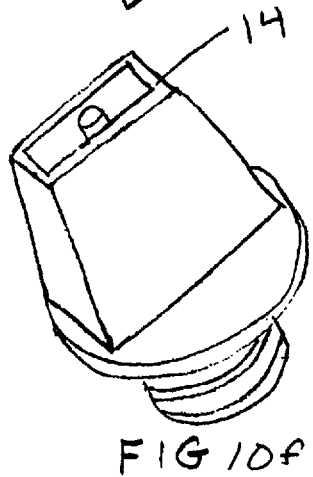

FIG. 10f depicts a further alternate embodiment wherein the tip cap 10 according to the present invention has a polygonal, rectangular top wall. 14, to provide an easily gripped surface for the user to impart torque to the tip cap 10. As will be apparent to one skilled in the art, the dimension of the rectangular top wall can be varied to, for example, increase the size of the gripping surface and other polygonal configurations can be used. Furthermore, the polygonal surface of the top wall 14, provides the user with a surface to impart force perpendicular to the rotational axis tangent.

While the preferred embodiments of the present invention have been described so as to enable one skilled in the art to practice the device of the present invention, it is to be understood that variations and modifications may be employed without departing from the concept and intent of the present invention as defined in the following claims. For example, the top wall shape can be varied by increasing or decreasing the major and minor axes. Alternately, the top wall could be other non-circular shapes, which are preferably elongated, such as, for example, rectangular. Accordingly, the preceding description is intended to be exemplary and should not be used to limit the scope of the invention. The scope of the invention should be determined only by reference to the following claims.

What is claimed is:
1. A tip cap comprising:
   a sealing base comprising a substantially flat surface having an upper surface defining a plane and a lower surface,
   a body having an elongated, non-circular shaped top wall, said body extending from said upper surface in a first direction with respect to the sealing base, said body having a non-circular elliptical cross-section when viewed at an angle substantially perpendicular to said upper surface, wherein the body of the tip cap has a major axis and a minor axis, wherein the major axis and the minor axis extend in a parallel direction with respect to the sealing base, wherein the major axis is greater than the minor axis, wherein an intersection of the major axis and minor axis defines a rotational center point about which the tip cap rotates, and wherein the non-circular shaped top wall allows a user to grasp and apply a rotational force to the tip cap without having to simultaneously provide a gripping force to the tip cap, and a shaft extending from said lower surface, said shaft having a wall defining a hollow portion and wherein the shaft includes an opening at a bottom end, the shaft extending in a second direction with respect to the sealing base and wherein the second direction is opposite from the first direction.

2. The tip cap of claim 1, wherein said non-circular section is comprised of a pair of arcuate structures.

3. The tip cap of claim 1, wherein said non-circular section is comprised of a plurality of cylindrical structures arranged around the central axis of said tip cap.

4. The tip cap of claim 1, wherein said top wall includes a textured surface.

5. The tip cap of claim 4, wherein said textured surface includes a plurality of dimples.

6. The tip cap of claim 1, wherein said shaft is joined to the lower surface of the sealing base and is configured to cooperate with a connector on a syringe to connect said tip cap to the syringe.

7. The tip cap of claim 6, wherein said top wall is joined to the upper surface of the sealing base and is configured to receive a force imparted thereto to cause the tip cap to rotate with respect to the syringe.

8. The tip cap of claim 1, wherein the top wall of the body is coextensive with the sealing base of the tip cap along the major axis of the body and wherein portions of the sealing base extend radially outwardly with respect to the top wall along the minor axis of the body, said portions of the sealing base extending outwardly with respect to the top wall along the minor axis of the body being configured to act as a shield against excessive downward movement of a user's fingers relative to the tip cap.

9. The tip cap of claim 1, wherein said shaft is shaped internally to releasably receive and contact a luer tip of a syringe and shaped externally to cooperate with a connector on the syringe.

10. The tip cap of claim 1, wherein the elongated top wall is configured to enable the user to grasp the tip cap at various points at a predetermined distance from the rotational center point measured along the major axis such that upon application of a rotational force to the tip cap, the top wall acts as a lever arm during rotation of the tip cap.

11. The tip cap of claim 1, wherein said body comprises a tubular member having an open portion facing the first direction with respect to the sealing base.

12. The tip cap of claim 1, wherein the hollow portion in the shaft extending from said lower surface of the sealing base comprises a well that is internally shaped to match a general shape of a syringe tip or luer, said well having an inner end having a generally flat profile and an external surface that is generally conical and extending in the first direction with respect to the sealing base.

13. A syringe assembly comprising:

a syringe comprising a barrel and a syringe tip extending from said barrel; and a tip cap for sealingly covering said syringe tip and comprising:

a sealing base comprising a substantially flat surface having an upper surface defining a plane and a lower surface, a body having an elongated, non-circular shaped top wall, said body extending from said upper surface in a first direction with respect to the sealing base, said body having a non-circular cross-section when viewed at an angle substantially perpendicular to said upper surface, wherein the body of the tip cap has a major axis and a minor axis, wherein the major axis and the minor axis extend in a parallel direction with respect to the sealing base, wherein the major axis is greater than the minor axis, wherein an intersection of the major axis and minor axis defines a rotational center point about which the tip cap rotates, and wherein the non-circular shaped top wall allows a user to grasp and apply a rotational force to the tip cap without having to simultaneously provide a gripping force to the tip cap, and a shaft extending from said lower surface, said shaft extending in a second direction with respect to the sealing base and wherein the second direction is opposite from the first direction, said shaft having connection means for attaching to said syringe tip.

14. The syringe assembly of claim 13, wherein the exterior of said top wall further includes a textured surface.

15. The syringe assembly of claim 14, wherein said textured surface includes a plurality of dimples.

16. The syringe assembly of claim 14, wherein said textured surface includes a plurality of radially extended flanges.

17. The syringe assembly of claim 13, wherein a recessed well extends at least partially through said lower surface of said base portion.

18. The syringe assembly of claim 17, wherein, said syringe tip at least partially extends into said well with said tip cap covering said syringe tip of said syringe.

19. The syringe assembly of claim 13, wherein said non-circular cross-section is rectangular.

20. The syringe assembly of claim 13, wherein said non-circular section is comprised of a pair of arcuate structures.

21. The syringe assembly of claim 13, wherein said non-circular section is polygonal.

22. The syringe assembly of claim 13, wherein said non-circular section is comprised of a plurality of cylindrical structures arranged around the central axis of said tip cap.

* * * * *